(12) United States Patent
Wingfield et al.

(10) Patent No.: US 11,547,116 B2
(45) Date of Patent: Jan. 10, 2023

(54) METAL OXIDE COMPOUNDS AND INFUSION INTO POLYMER COMPOUNDS

(71) Applicants: William Wingfield, Richmond, VA (US); Guerry L Grune, Virginia Beach, VA (US); Richard L Mason, University Park, FL (US)

(72) Inventors: William Wingfield, Richmond, VA (US); Guerry L Grune, Virginia Beach, VA (US); Richard L Mason, University Park, FL (US)

( * ) Notice: Subject to any disclaimer, the term of this patent is extended or adjusted under 35 U.S.C. 154(b) by 2228 days.

(21) Appl. No.: 14/652,371

(22) PCT Filed: Dec. 13, 2013

(86) PCT No.: PCT/US2013/000273
§ 371 (c)(1),
(2) Date: Jun. 15, 2015

(87) PCT Pub. No.: WO2014/092747
PCT Pub. Date: Jun. 19, 2014

(65) Prior Publication Data
US 2015/0351406 A1 Dec. 10, 2015

Related U.S. Application Data

(60) Provisional application No. 61/736,089, filed on Dec. 12, 2012.

(51) Int. Cl.
| | | |
|---|---|---|
| *A61K 8/19* | (2006.01) | |
| *A61K 33/00* | (2006.01) | |
| *A01N 55/02* | (2006.01) | |
| *A01N 25/02* | (2006.01) | |
| *A23B 4/22* | (2006.01) | |
| *A01N 59/16* | (2006.01) | |
| *A61K 33/24* | (2019.01) | |
| *A61K 33/38* | (2006.01) | |
| *A61K 33/34* | (2006.01) | |
| *A61K 31/765* | (2006.01) | |
| *A61K 33/30* | (2006.01) | |
| *A01N 59/20* | (2006.01) | |
| *A61K 8/73* | (2006.01) | |

(Continued)

(52) U.S. Cl.
CPC ............. *A01N 55/02* (2013.01); *A01N 25/02* (2013.01); *A01N 25/22* (2013.01); *A01N 59/16* (2013.01); *A01N 59/20* (2013.01); *A23B 4/22* (2013.01); *A23L 3/34635* (2013.01); *A61K 8/0241* (2013.01); *A61K 8/19* (2013.01); *A61K 8/345* (2013.01); *A61K 8/736* (2013.01); *A61K 31/765* (2013.01); *A61K 33/00* (2013.01); *A61K 33/24* (2013.01); *A61K 33/242* (2019.01); *A61K 33/243* (2019.01); *A61K 33/244* (2019.01); *A61K 33/30* (2013.01); *A61K 33/34* (2013.01); *A61K 33/38* (2013.01); *A61Q 17/005* (2013.01); *A61Q 19/00* (2013.01); *A23B 4/24* (2013.01); *A23V 2002/00* (2013.01); *A61K 2800/10* (2013.01); *A61K 2800/51* (2013.01); *A61K 2800/58* (2013.01)

(58) Field of Classification Search
CPC ........ A01N 25/04; A01N 59/16; A01N 59/20; A01N 25/02; A01N 25/22; A01N 55/02; A23V 2002/00; A61K 2800/10; A61K 2800/51; A61K 2800/58; A61K 31/765; A61K 33/00; A61K 33/24; A61K 33/30; A61K 33/34; A61K 33/38; A61K 8/0241; A61K 8/19; A61K 8/345; A61K 8/736; A61K 33/242; A61K 33/243; A61K 33/244; A61Q 17/005; A61Q 19/00
See application file for complete search history.

(56) References Cited

U.S. PATENT DOCUMENTS

| | | | |
|---|---|---|---|
| 4,592,920 | A | 6/1986 | Murtfeldt et al. |
| 4,677,143 | A | 6/1987 | Laurin et al. |

(Continued)

FOREIGN PATENT DOCUMENTS

| | | |
|---|---|---|
| RU | 2271814 C2 | 3/2006 |
| RU | 2314796 C2 | 1/2008 |

(Continued)

OTHER PUBLICATIONS

Porramezan et al. (Composites: Part B 42 (2011): 1980-1986). (Year: 2011).*

(Continued)

*Primary Examiner* — Ernst V Arnold
(74) *Attorney, Agent, or Firm* — ePatentManager.com; Guerry L. Grune

(57) ABSTRACT

Described is an initial liquid composition with at least antimicrobial, antibacterial, and/or anti-viral properties comprising chelated metal oxide particles suspended in a polyol, such that metal oxide particles are homogeneously dispersed in a primarily liquid based polyol carrier so that chelated metal oxide particles form a stable complex suspension that is optionally an alkaline based aqueous silver oxide dispersion. The liquid composition can be subsequently added to any polymer or polymer compound/system where the polymer degrades or melts at a temperature lower than the polyol carrier degradation or boiling temperature. The metal oxide complex may also impart beneficial semi-conductive or conductive as well as permeability and flammability property changes to the polymer (host) system.

17 Claims, 3 Drawing Sheets

(51) Int. Cl.
*A61K 8/34* (2006.01)
*A61Q 19/00* (2006.01)
*A61Q 17/00* (2006.01)
*A61K 8/02* (2006.01)
*A61K 33/242* (2019.01)
*A61K 33/244* (2019.01)
*A61K 33/243* (2019.01)
*A01N 25/22* (2006.01)
*A23L 3/3463* (2006.01)
*A23B 4/24* (2006.01)

(56) References Cited

U.S. PATENT DOCUMENTS

| | | |
|---|---|---|
| 4,847,049 A | 7/1989 | Terry |
| 4,849,223 A | 7/1989 | Pratt et al. |
| 4,933,178 A | 6/1990 | Capelli et al. |
| 5,019,096 A | 5/1991 | Fox, Jr. et al. |
| 5,676,977 A | 11/1997 | Antelman et al. |
| 5,848,995 A | 12/1998 | Walder |
| 5,895,782 A | 4/1999 | Overton et al. |
| 6,258,385 B1 | 7/2001 | Antelman et al. |
| 6,583,176 B2 | 6/2003 | Arata |
| 6,716,895 B1 | 4/2004 | Terry |
| 6,756,059 B2 | 6/2004 | Terry |
| 6,881,421 B1 | 4/2005 | da Silveira et al. |
| 6,949,598 B2 | 9/2005 | Terry |
| 7,135,195 B2 | 11/2006 | Holladay et al. |
| 7,179,849 B2 | 2/2007 | Terry |
| 7,311,927 B2 | 12/2007 | Miner et al. |
| 7,378,156 B2 | 5/2008 | Terry |
| 8,034,454 B2 | 10/2011 | Terry |
| 9,132,296 B2 * | 9/2015 | Wingfield ................ A61Q 5/02 |
| 9,393,261 B2 * | 7/2016 | Sternoff ................ A61K 8/4946 |
| 10,687,535 B2 * | 6/2020 | Wingfield ............ A61K 33/242 |
| 2004/0022868 A1 | 2/2004 | Antelman et al. |
| 2006/0105057 A1 | 5/2006 | Antelman et al. |
| 2008/0311206 A1 | 12/2008 | Student et al. |
| 2010/0120915 A1 | 5/2010 | Beierle |
| 2010/0203088 A1 * | 8/2010 | Sanjeev ................... A61K 9/14 424/400 |
| 2013/0022643 A1 * | 1/2013 | Sternoff ................. A61Q 17/00 424/400 |

FOREIGN PATENT DOCUMENTS

| | | |
|---|---|---|
| WO | 2006074359 A2 | 7/2006 |
| WO | 2006064387 C2 | 9/2006 |

OTHER PUBLICATIONS

"Gel" ([online] Britannica retrieved on Nov. 2, 2021 from: https://www.britannica.com/science/gel; 1 page). (Year: 2021).*

* cited by examiner

Figure 1: TGA Plot for Chelated Silver Oxide in Glycerine at 4000 ppm AgO

| 10 | Prepare Chitosan |
|----|----------------------|
|    |                      |
| 11 | Provide raw material |
| 12 | Remove non-chitin components |
| 13 | Dry and grind to desired size |
| 14 | Deacetylation |
| 15 | Rinse |

FIG. 2

| 20 | Prepare Chitosan Solution |
|----|-------------------------------|
|    |                               |
| 21 | Provide deionized water |
| 22 | Provide Chitosan powder |
| 23 | Provide alpha-hydroxy acid |
| 24 | Mix |

FIG. 3

| 30 | Prepare Aqueous Silver Solution |
|----|-------------------------------------|
|    |                                     |
| 31 | Provide silver salts                |
| 32 | Provide alkaline solution           |
| 33 | Create silver oxide                 |
| 34 | Provide carboxylic acid             |
| 36 | Provide deionized water             |
| 37 | Provide light impervious container  |

FIG. 4

| 40 | Prepare Antimicrobial Complex |
|----|-----------------------------------|
|    |                                   |
| 41 | Provide Chitosan Solution         |
| 42 | Provide deionized water           |
| 43 | Provide Aqueous Chelated Silver Solution |
| 44 | Mix until homogenous              |

FIG. 5

METAL OXIDE COMPOUNDS AND INFUSION INTO POLYMER COMPOUNDS

This application claims priority to and benefit from PCT application PCT/US2013/000273, entitled "Metal Oxide Compounds and Infusion into Polymer Compounds" filed Dec. 13, 2013 which claims priority to and benefit from U.S. Provisional application 61/736,089, entitled "Metal Oxide Compounds and Infusion into Polymer Compounds" filed Dec. 12, 2012. Priority is also claimed to 60/930,535, filed May 17, 2007 and the corresponding U.S. nonprovisional application Ser. No. 12/157,712, filed May 16, 2008, both entitled "Antimicrobial Solution and Methods of Making and Using the Same" and assigned to William Wingfield. This application also claims priority to U.S. nonprovisional application Ser. No. 13/188,630, filed on Jul. 22, 2012, entitled "Antimicrobial Anti-Chafing Chelated Silver Oxide Compound" and the corresponding PCT application, PCT/US2012/047854, filed Jul. 23, 2012 of the same title. This application also incorporates by reference the entire contents of all above referenced applications.

FIELD OF THE INVENTION

The present invention relates to an antimicrobial, antibacterial, anti-viral, antifungal, UV resistant, at least semi-conductive, gas permeability and flammability changing substance which includes a chelated metal oxide complex, and in particular, a chelated silver oxide suspended in a polyol. Adding this complex directly into bio-based or petroleum based thermoplastic polymers is also a key feature of the application. More specifically, the present disclosure describes adding the polyol based chelated silver oxide into ethylene vinyl acetate (EVA) copolymers as well as adding to acrylic paints. This process and the resulting compounds create complexed chelated metal (in this case at least silver) oxide based antimicrobial polymeric compounds, articles of manufacture using these compounds and methods of making the same. The same polymeric compounds also possess UV resistant, semi-conductive/conductive, gas permeability, and flammability changing properties without substantially affecting (reducing the values) the physio-chemical properties of the host polymer system.

As mentioned, this disclosure also provides for use of the polyol chelated metal oxide complex, which is formed in the liquid state to be used in combination with essentially any other fluid (including gases or liquids) to impart the special properties associated with the same chelated metal oxide. The polyol chelated metal oxide complex acts as a carrier for essentially any host that is compatible with the polyol. The polyols of the present disclosure are versatile and can be incorporated into at least liquids and solids that are stabile up to the decomposition temperature of the polyol. In some cases, the polyols may also be useful as a carrier in a gaseous phase of the desired composition.

BACKGROUND OF THE INVENTION

For many years silver and silver salts have been used as antimicrobial agents. Early medicinal use of silver was the application of aqueous silver nitrate solutions to prevent eye infection in newborn babies. Silver salts, colloids, and complexes have also been used to prevent and to control infection. For example, colloidal metallic silver has been used topically for dermatitis, conjunctivitis, and infections including vaginal infections.

Other metals, such as gold, zinc, copper and cerium, have also been found to possess antimicrobial properties, both alone and in combination with silver. These and other metals have been shown to provide antimicrobial behavior even in extremely low concentrations, a property referred to as "oligodynamic." Metal ions, especially those of heavy metals, show this effect. The exact mechanism of action is still unknown. Data from silver suggest that these ions denature enzymes of the target cell or organism by binding to reactive groups, resulting in their precipitation and inactivation. There is recent evidence of changing the cellular DNA structure itself. Silver also reacts with the amino-, carboxyl-, phosphate-, and imidazole-groups and diminish the activities of lactate dehydrogenase and glutathione peroxidase. Bacteria are in general affected by the oligodynamic effect and it seems this effect is agnostic with regard to the strain of bacteria. Viruses in general are not as sensitive to this effect.

Silver is a naturally occurring element that is present in our environment, including the air we breathe, the water we drink and the foods we consume. However, silver does not occur naturally in the tissues of humans and animals. Silver exhibits relatively low toxicity to animals and humans. It is however, extremely toxic to simpler forms of life such as bacteria. The antibacterial properties of silver are known, and were at least suspected for thousands of years. The ancient Greeks used silver pots and other utensils. Hippocrates, the father of modern medicine, wrote that silver had beneficial healing and anti-disease properties. The Phoenicians stored water, wine and vinegar in silver bottles to prevent spoiling. In the early 1900s, it was not uncommon for people to place silver dollars in milk bottles to prolong the freshness of the milk. The malleability and non-toxicity of silver make it a useful material used in dental alloys for fittings and fillings.

Widespread use of silver declined with the development of modern antibiotics, many of them used to kill pathogens, but overuse has led to increased bacteria resistance. Hence, there is renewed interest in silver as a broad spectrum antimicrobial. Silver, when applied topically, demonstrates efficacy against microorganisms which sometimes exhibit resistance characteristics. There are many products on the market to treat or kill bacteria. These products are found in a variety of forms, including liquid, foam, gel, lotions and ointments.

Additionally, silver is known for antimicrobial use with dental and medical devices, such as mouthpieces, mouthguards, dental appliances, as well as catheters, cannulae, and stents. Additionally, silver compounds have been used in fluids for consumption and incorporated into both clothing and packaging for prevention of infections, bacterial growth, and spoilage.

Hospital acquired infections due to bacteria cause approximately more than 100,000 deaths annually. This number is more than the combined death total resulting from AIDS, breast cancer and automobile accidents. The economic burden is estimated to be greater than $5.2 billion annually. These infections are the fourth leading cause of death. Inadequate hand hygiene also contributes to food-related illnesses, including *salmonella* and *E. coli* infection. According to The Center for Disease Control and Prevention (hereafter, the "CDC"), as many as 76 million Americans contract a food-borne illness each year. Of these, nearly 5,000 die as a result of the illness. Others experience the annoying symptoms of nausea, vomiting and diarrhea.

Published CDC guidelines enhanced hand sanitizer sales in the United States, which experienced double-digit growth in the 2004-2010 period, according to marketing information provided by A. C. Nielsen. The total annual U.S. infection prevention industry is estimated to be $9.4 billion.

One conventional approach for obtaining antimicrobial products is via the deposition of metallic silver directly onto the surface of the substrate, for example, by vapor coating, sputter coating, or ion beam coating. However, these non-contact deposition coating techniques suffer many drawbacks. These drawbacks include poor adhesion, lack of coating uniformity, and the need for special processing conditions, such as preparation in darkness due to the light sensitivity of some silver salts. One particular drawback of these coatings is that the processes by which the coatings are formed do not adequately coat hidden or enclosed areas. Additionally, these methods produce coatings that are very much like metallic silver in that they do not release silver from the coating and require contact with the coating to provide antimicrobial action. Though high concentrations of silver may be deposited on the substrate, very little free ionic silver is released on exposure to aqueous fluid. As a result, these coatings provide only limited antimicrobial activity. They essentially retard colonization of microbial agents on the surface of the device. However, because they do not release sufficient silver ions into aqueous fluids, they offer little or no protection from bacteria carried onto or into mammalian bodies and do not inhibit infection in surrounding areas.

Another method of coating silver onto a substrate involves deposition or electrodeposition of silver from solution. Drawbacks of these methods include poor adhesion, low silver pick-up on the substrate, the need for surface preparation, and high labor costs associated with multistep dipping operations usually required to produce the coatings. Adhesion problems have been addressed by inclusion of deposition agents and stabilizing agents, such as gold and platinum metals, or by forming chemical complexes between a silver compound and the substrate surface. However, inclusion of additional components increases the complexity and cost of producing such coatings.

With many devices, it is preferred to have a lubricious coating on the device. Lubricious coatings aid device insertion, reduce the trauma to tissue, and reduce the adhesion of bacteria. Another drawback to conventional methods which apply silver and other metals directly onto the surface of a device for which a lubricious coating is also desired is that a second, lubricious coating must be applied to the device over the antimicrobial coating, adding to manufacturing cost and time.

Some of these coatings release, to varying degrees, silver ions into the solution or tissue surrounding the substrate. However, activation of such coatings often requires conditions that are not suitable for use with dental or medical devices or are not even suitable as protectorants for food and clothing.

Another conventional approach for obtaining antimicrobial medical devices is the incorporation of silver, silver salts, and other antimicrobial compounds into the polymeric substrate material from which the article is formed. An oligodynamic metal may be physically incorporated into the polymeric substrate in a variety of ways. For example, a liquid solution of a silver salt may be dipped, sprayed or brushed onto the solid polymer, for example, in pellet form, prior to formation of the polymeric article. Alternatively, a solid form of the silver salt can be mixed with a finely divided or liquefied polymeric resin, which is then molded into the article. Further, the oligodynamic compound can be mixed with monomers of the material prior to polymerization.

There are several disadvantages to all of these approaches. One such disadvantage is that larger quantities of the oligodynamic material are required to provide effective antimicrobial activity at the surface of the device. A second disadvantage is that it is difficult to produce articles that allow for the release of the oligodynamic material because most device polymers absorb little, if any, water to aid in the diffusion and release of the oligodynamic material, resulting in articles that provide only a limited antimicrobial effect.

Yet another approach for obtaining antimicrobial devices is the incorporation of oligodynamic agents into a polymeric coating which is then applied to the surface of the article. Typically, an oligodynamic agent is incorporated into the coating solution in the form of a solution or a suspension of particles of the oligodynamic agent. Problems associated with this approach include poor adhesion of the coating to the substrate, settling and agglomeration of the oligodynamic particles, and inadequate antimicrobial activity over time.

Settling of particles of the oligodynamic agent occurs as a result of the size and density of the particles. Settling of the particles from such solutions can cause unpredictable changes in the concentration of the oligodynamic agent in the composition. These changes in ion concentration result in several drawbacks for producing commercial products. First, unpredictable changes in the concentration of the oligodynamic agent make it difficult to produce a composition having a specific, homogenous, exact concentration of antimicrobial ions and, thus, a particular and specific effectiveness. Additionally, these changes make it difficult to produce multiple batches of the composition having the same antibacterial concentration. Furthermore, the concentration of the antimicrobial ions can affect other properties of the composition, such as its adhesive and lubricious properties. Consistency of antimicrobial activity is essential in the production of antimicrobial devices.

Another problem associated with particle suspensions is agglomeration of the particles. Particle agglomeration produces larger particle sizes which increases settling of particles from solution. Additionally, the agglomeration of particles in suspensions and coating solutions can produce particles in the coating that are large enough to be noticeable to the touch on the coated surface. Articles produced using such coatings have decreased patient comfort and, therefore, are undesirable.

Many researchers have attempted to overcome these problems. For example, U.S. Pat. No. (herein after "U.S. Pat. No.") 4,592,920 to Murtfeldt et al. discloses a process that attempts to overcome the settling and agglomeration problems in the art through the use of a comminuted metal having a particle size of 30 microns or less. The coating of the Murtfeldt patent, however, exhibits several disadvantages. For example, the Murtfeldt coating exhibits poor adhesion which is overcome by the use of the following methods. First, the Murtfeldt patent recommends pretreatment of the catheter to leach undesirable compounds that interfere with the bonding of the coating to the surface of the catheter. Second, the Murtfeldt patent recommends the use of a bridging compound, or primer, to attach the coating to the surface of the catheter to increase adhesion. This adds an additional manufacturing step to the fabrication of a coated device. In addition to these disadvantages, it is likely that the process used to manufacture and coat the catheters in Murtfeldt will result in settling and agglomeration problems even with the use of silver having smaller particle sizes.

U.S. Pat. No. 4,849,223 to Pratt et al. attempts to overcome settling and agglomeration of the particles in his invention by using solutions that contain high concentrations of polymer or monomer solids and are, thus, viscous. Suspending particles in high viscosity coating solutions containing high polymer solids is a common method for reducing settling and agglomeration of the particles. The coatings made by this method are usually very thick and, as a result, are often not uniform. Thick coatings are also more costly, dry more slowly than thin coatings, and are more difficult to manufacture. The coatings of the Pratt patent also exhibit poor adhesion. To increase adhesion, the Pratt patent recommends using coating materials which are similar to the substrate to be coated, pretreating the surface of the substrate before the coating composition is applied, or applying an additional coating layer between the substrate and the coating.

U.S. Pat. No. 5,019,096 to Fox, Jr. et al. discloses a method for increasing the antibacterial activity of silver by incorporating a synergistic amount of chlorhexidine and a silver salt in a matrix-forming polymer. The polymer is such that it allows for release of the antimicrobial agent over an extended period of time. Fox, however, relies on dispersation of silver particles into coating solutions and will be susceptible to problems associated with particle settling and agglomeration.

U.S. Pat. No. 4,677,143 to Laurin et al. discloses a method to enhance release of the antimicrobial metal ions from the surface of a device by incorporating the antimicrobial metal into a binder having a low dielectric constant that coats or forms the device. The nature of the binder allows the particles to form chain-like structures among themselves. These chain-like structures allow the surface particles to dissolve to provide an initial dose of the antimicrobial agent and to create a pathway for interior particles to come to the surface to provide additional doses of the antimicrobial agent over time. Laurin, however, also relies on dispersation of silver particles into coating solutions and is susceptible to problems associated with particle settling and agglomeration.

U.S. Pat. No. 4,933,178 to Capelli discloses a polymer coating containing an oligodynamic metal salt of a sulfonylurea. The Capelli patent attempts to improve the solubility and stability of the antimicrobial metal in the coating and to provide for the sustained release of the antimicrobial agent by adding a carboxylic acid to the coating composition. The particular carboxylic acids and the proportions in which they are mixed determine the rate of release of the antimicrobial agent from the polymer coating composition.

U.S. Pat. No. 5,848,995 to Walder discloses the solid phase production of polymers containing AgCl as an antimicrobial agent. In the Walder process, solid polymer pellets are first soaked in a solution of silver nitrate which is absorbed into the pellets. The pellets are then rinsed, dried, and soaked in a solution of a sodium chloride. The chloride ions of the salt are absorbed into the polymer matrix of the pellets where they react with the silver nitrate to form silver chloride. The pellets are then rinsed, dried, and melt processed. The compositions of the Walder patent are limited to hydrophilic polymers, must be thermoformed, and do not contain other silver salts to provide multiple release rates, or other oligodynamic or medicinal agents to enhance antimicrobial effectiveness.

U.S. Pat. Nos. 6,716,895, 6,949,598, 7,179,849, 7,378,156, and 8,034,454 to Terry, describe another method for preparing antimicrobial medical devices where colloidal metal oxides such as silver oxide are prepared as colloids and dispersed into or onto polymer systems as coatings.

U.S. Pat. No. 4,847,049 to Yamamoto and entitled "Method of Forming Chelated Collagen Having Bactericidal Properties" describes a method for protecting renatured collagen against bacterial and fungal attack. The method includes contacting the collagen with a silver ion containing solution at a pH range of 4.0 to 9.0 and exposing the silver-chelated collagen to ultraviolet radiation.

U.S. Pat. No. 6,756,059 to Rozell et al. and entitled "Topical Composition, Topical Composition Precursor, and Methods for Manufacturing and Using" discloses a topical composition precursor prepared by melt processing a hydrophobic polymer composition that includes repeating pyrrolidone/alkylene groups wherein the alkylene groups contain at least 10 carbon atoms, and a hydrophobic polymer composition including repeating carboxylic groups and/or hydroxyl groups.

U.S. Pat. No. 6,716,895 to Terry entitled "Polymer Compositions Containing Colloids of Silver Salts" teaches how to provide varying release kinetics for the active ions in the compositions due to different water solubilities of the ions, allowing antimicrobial release tailored to a given application. The polymer compositions are stated to contain colloids comprised of salts of one or more oligodynamic metals such as silver.

U.S. Pat. No. 7,135,195 to Holladay et al. entitled "Treatment of Humans with Colloidal Silver Composition" describes water and silver particles, wherein the silver particles comprise an interior of elemental silver and an exterior of ionic silver oxide. The silver particles are described to be present in the water at a level of about 5-40 parts per million (Hereafter, "ppm").

U.S. Pat. No. 6,881,424 to Kemp entitled "Highly Acidic Metalated Organic Acid" teaches how to mix a monovalent or polyvalent cation and an organic acid in the presence of a strong oxyacid. The resulting composition is described to be less corrosive to a ferrous metal than a solution of a mineral acid having the same acidic pH value, and is more biocidal than a mixture of the organic acid and a metal salt of the organic acid which mixture has the same acid normality value.

U.S. Pat. No. 5,895,782 to Overton et al. is entitled "Acid Replacement Solution for Cleaning of Non Ferrous Metals" describes the use of non-ferrous alloys such as copper, brass and high strength aluminum alloys for cleaning purposes. The solution is described to be prepared by mixing $Ca(OH)_2$ and KOH with equivalent sulfuric acid in water, and then passing the solution through a 10 micron filter.

U.S. Pat. No. 6,383,095 to Newman, et al. is entitled "Ionic Silver Complex" and describes how to combine ingredients including water, a source of free silver ions, and a substantially non-toxic, substantially thiol-free, substantially water soluble complexing agent. This patent claims the use of an alkali metal and/or alkaline earth metal used as a counter-ion.

U.S. Pat. No. 6,583,176 to Arata is entitled "Aqueous Disinfectant" and describes an aqueous solution that is formulated by electrolytically generating silver ions in water in combination with a citric acid.

Japanese patent application JP 2007230996A2 (Abstract only) and entitled "Anti-chafing composition comprising Boron Nitride" to General Electric Co., describes an anti-chafing composition for topical application comprising boron nitride.

US Patent Application No. 20080311206A1 entitled "Anti-Chafing Compositions Comprising Boron Nitride" to Student, et al. and assigned to General Electric Co., describes an anti-chafing composition for topical application comprising boron nitride.

U.S. Pat. No. 5,676,977 entitled "Method of Curing AIDS with Tetrasilver Tetroxide Molecular Crystal Devices" to Antelman and assigned to Antelman Technologies Ltd. describes a method of curing the AIDS virus using an intravenous injection using Tetrasilver Tetroxide.

Korean Patent Application KR7090732A—entitled "Anti-chafing compositions comprising Boron Nitride" to Student, et al. and assigned to General Electric Co., describes an anti-chafing composition for topical application.

U.S. Pat. No. 6,258,385 entitled "Tetrasilver Tetroxide Treatment for Skin Conditions to Antelman and assigned to Marantech Holding, LLC describes an invention that relates to the use of electron active molecular crystals comprising tetrasilver tetroxide (Ag4O4) for the treatment and cure of dermatological skin conditions.

US Application Number US20060105057 entitled "Compositions Using Tetrasilver Tetroxide and Methods for Management of Skin Conditions Using Same" to Antelman and assigned to Marantech Holding, LLC., describes pharmaceutical compositions including tetrasilver tetroxide (Ag4O4), such as in crystalline form, and methods of using such compositions for the prevention, treatment, and management of various dermatological skin conditions and diseases to include but not limited to skin chafing.

US Application Number US20040022868 entitled "Compositions Using Tetrasilver Tetroxide and Methods for Management of Skin Conditions Using Same" to Antelman and assigned Marantech Holding, LLC describes pharmaceutical compositions including tetrasilver tetroxide (Ag4O4), such as in crystalline form, and methods of using such compositions for the prevention, treatment, and management of various dermatological skin conditions and diseases to include but not limited to skin chafing.

US Application Number 20100120915A1 entitled "Antimicrobials and Related Methods to Beierle and not assigned, describes antimicrobial balms but does not mention the use of any type of silver or silver ions).

U.S. Pat. No. 7,311,927 entitled "Antiseptic Solutions Containing Silver Chelated with Polypectate and EDTA" to Miner, et al and assigned to Edwin Odell Miner, describes a liquid antiseptic and cleanser having improved long-term stability and includes silver ion in the list of ingredients.

PCT Publication Number WO2004/028461 entitled "Antiseptic Solutions Containing Silver Chelated with Polypectate and EDTA" by Miner, et al, describes a liquid antiseptic and cleanser having improved long-term stability and includes silver ions in the list of ingredients.

A PCT application to Karandiakar, WO 2006/015317, entitled "Antimicrobial Devices and Compositions" describes methods and compositions for antimicrobial devices comprising metal containing compositions which are resistant to heat and light discoloration. The metal containing compositions may comprise salts or complexes of silver, copper or zinc. In one aspect the compositions comprise silver salts. In another aspect, the compositions comprise silver complexes. In one aspect, the metal salts may comprise metal salts of saccharin, acesulfame, long chain fatty acids, and alkyl dicarboxylic acids. The compositions further comprise polymers which form salts or complexes with silver, copper or zinc. The methods of the present invention comprise treating devices with the metal containing compositions, including, but not limited to, such devices as woven wound care materials, catheters, patient care devices, and collagen matrices. A US patent to Newman, U.S. Pat. No. 6,830,895, entitled "Ionic Silver Oxide Complex" describes an invention that relates to a substantially non-colloidal solution made by combining ingredients comprising (a) water; (b) a source of free silver ions; and (c) a substantially non-toxic, substantially thiol-free, substantially water-soluble complexing agent.

Therefore, a need has been established to provide a method for rendering articles resistant to infection by reducing or eliminating undesirable bacteria growth, not only on the surface of the article but throughout the article so that the metal oxide complex is homogenously dispersed and endures throughout the life of the use of the article. There is also a need in the art for metal oxide compositions which can be incorporated into articles to provide antimicrobial activity. There is also a need for compositions that overcome the solubility, settling, and agglomeration problems of conventional oligodynamic compositions, and exhibit enhanced, sustained release of oligodynamic agents when these agents (primarily silver oxide for the present disclosure, but copper and other metal oxides are also useful) are dispersed within certain polymer systems. Incorporating the metal oxides into these articles in a cost efficient and reproducible manner, is required for providing readily available items of manufacture and one subject of the present disclosure.

SUMMARY OF THE INVENTION

Stated generally, the present invention comprises antimicrobial compositions which provide the advantage of reduced or elimination of settling and agglomeration by providing chelated metal oxide particles in a liquid homogenous dispersed suspension producing a minimal particle size of the oligodynamic metal oxides in the composition. These particles remain suspended indefinitely in the liquid dispersion in that they generally do not precipitate out of solution. The liquid portion of the solution is comprised primarily of a polyol and more specifically a glycerol and most specifically glycerine (vegetable or petroleum based). The use of metal oxide chelation in these compositions also permits incorporation of higher and more stable concentrations of these metal oxide particles without the difficulties associated with the suspensions described in the related art. These higher concentrations are important so that, eventually relatively lower (let down) concentrations of the chelated metal oxide dispersed suspensions can be added to polymeric resins (normally in the beginning in the form of pellets) or injected directly during heat and or pressure compounding, and/or molding, and/or extrusion. The resultant composition is a combination of a polymeric resin and chelated metal oxide that can be repelletized with or without colorant, flavoring, and additional additives for eventual extrusion or molding or other thermal/pressure forming of any thermoplastic where the "host" thermoplastic has a melting or decomposition temperature below that of the polyol. The thermoplastic must be miscible and/or compatible with the polyol/glycerine based chelated metal oxide suspension so that combining of the polymer with the suspension leads to either a processible final compound or can be injected directly to achieve anti-bacterial (and other desired) properties. In making these compounds or final articles of manufacture, it has been proven to also add colorants (primarily azo compounds) without interfering (altering the properties significantly) with either the final anti-bacterial or physio-chemical properties of the eventual article of manufacture.

One particularly useful embodiment specifically provides an antimicrobial, antibacterial, and/or anti-viral, (as well as semi-conductive, inflammability, and reduced permeability) liquid composition comprising; chelated metal oxide particles suspended in a polyol, wherein the metal oxide particles are homogeneously dispersed in the liquid and wherein the chelated metal oxide particles form a stable complex suspension that is often initially an alkaline based aqueous silver oxide dispersion complexed with a carboxylic acid, wherein the resulting metal oxide complex suspension is provided in a concentration of at least 0.001 weight percent in the liquid composition. The liquid composition is a stable suspension that does not form a precipitate. The liquid composition metal oxide complex is often most preferably silver oxide. The liquid composition of the polyol is often preferably glycerine. Further, the liquid composition can be an initially aqueous dispersion that is further complexed with a combination of chitosan and a carboxylic acid.

In a further useful embodiment, an antimicrobial, antibacterial, and/or anti-viral, polymeric composition comprises; chelated metal oxide particles homogeneously suspended in a polyol thereby creating a polyol chelated metal oxide complex suspension wherein the polyol complex is a carrier that is combined with a polymer host. The polymer host can be one of any of the polymers described herein. In providing the final product, the complex suspension can also be directly injected into the polymer during a molding operation. In so doing, it is apparent that compounding resin pellets that are subsequently heated and molded (or extruded or otherwise melt processible) is no longer a required step. Direct injection of the silver oxide (or other metal oxide) complex during mold injection (or other comparable molding/extrusion processes) requires the proper "let down ratios" be established to achieve the proper metal oxide concentration in the final product. Direct injection without compounding greatly reduces the cost of the final article of manufacture.

In another aspect, the compositions of the present invention provide the advantage of varying release kinetics for the active oligodynamic ions due to different solubilities of different chelated metal oxide salts in the compositions. These varying release kinetics allow for an initial release of oligodynamic ions that provide antimicrobial activity immediately upon use, followed by a continual, extended release of the oligodynamic ions from the composition, resulting in sustained antimicrobial activity over time.

Stated somewhat more specifically, the present invention relates to compositions that eventually comprise a polymer, and a chelated metal oxide of one or more oligodynamic agents. In one disclosed embodiment, the polymer is a hydrophilic polymer. In another disclosed embodiment, the polymer is a hydrophobic polymer, while in yet another embodiment, the polymer is a combination of these two types of polymers. The polymer maybe an oligomer, a copolymer, a terpolymer, etc. and may be a blend of any combination or derivative of these. In all cases, the polymer or associate derivatives must be miscible or compatible with a polyol and/or glycerine so that the chelated metal oxides can be compounded or blended into or with the polymer.

In yet another embodiment, antimicrobial, antimicrobial, and/or antiviral products manufactured comprise a polymeric composition and chelated metal oxide particles homogeneously suspended in a polyol combined and infused into a polymer of the polymeric composition including a polyol metal oxide complex in a concentration of at least 0.001 weight percent metal oxide infused within the polyol such that the concentration of the polyol metal oxide complex is no greater than 25 weight percent of the polymeric composition.

A further embodiment of this invention results in a composition comprising a silver oxide and water and/or glycerine chelated silver oxide solution together with a co-complexing bio-film former wherein the composition electrostatically binds with a negatively charged surface.

Embodiments of this invention are thereby achieved by the method of creating a metal oxide composition disclosed within, the steps of which comprise providing a chelated oxide complex with a concentration of at least 100 parts per million of silver oxide together with a polyol, which results in forming a chelated silver oxide polyol complex with a silver oxide concentration of at least 2 weight percent by mixing the chelated silver oxide complex with the polyol after the polyol has been heated and stirred together with the silver oxide complex at a temperature of at least 140 degrees Fahrenheit.

DETAILED DESCRIPTION

The Composition

In a first aspect, the present invention provides antimicrobial, antibacterial, and in some cases, anti-viral metal oxide complexes in primarily polyol based solutions forming stable homogenous chelated metal oxide complex suspensions resulting in minimal or no precipitate.

In a second aspect, the complex oligodynamic agent suspension is direct injected, mixed, blended, or compounded with a polymer. The term "oligodynamic agents" as used in the present invention refers in this case to any chelated metal oxide compound that provides an associated antimicrobial (or other desirable) characteristic or activity, even when present in relatively small quantities and low concentrations.

One preferred embodiment is that of a chelated silver oxide that is suspended in a polyol. The homogenous chelated metal (silver in one instance) oxide suspension is concentrated in the polyol solution to at least 4000 ppm (in glycerine). Higher initial concentrations with, for example, PEG, are possible. This highly concentrated chelated metal oxide solution is a complex suspension that is subsequently diluted as it is incorporated into essentially any polymer or other acceptable (miscible with the polyol carrier) liquid. This incorporation will impart the desirable properties of the chelated metal oxide into the host substrate without any intended or known undesirable physio-chemical property changes.

Any polymer may be employed in the present invention, including hydrophilic polymers, hydrophobic polymers, and mixtures of these two types of polymers. The use of hydrophilic polymers is preferred because such polymers have additional benefits. These benefits include increased lubricity for patient comfort, increased absorption of aqueous fluids from the body which aids in the release of oligodynamic ions from the composition, inhibition of bacterial attachment, and improved solubility for some metal salts. Hydrophilic polymers best suited to the invention are those that are soluble in water or in organic solvents containing water. The ability to add water to the polymer composition without precipitating the metal oxides is a added benefit but not a prerequisite of the present invention. Water facilitates the formation of salt colloids that may precipitate either before or after addition the polymers providing the final composition. For this reason, it is preferred that the polymer solution contain essentially no water by weight, and certainly no more than 5 to 30% water.

However, the use of water is not limiting, as metal oxide chelates can also be formed or suspended in alcohols, organic solvents, or both that contain little or no water. The use of alcohols and organic solvents, containing from 0 to 1% water are preferred when hydrophobic polymers are employed in the present invention. Activity of the chelated metal oxides will vary with the carrier they are employed within. Precipitation will also vary based on the initial concentration of the metal oxide capability within the complex suspension.

Examples of hydrophilic polymers which may be used to form the compositions include, but are not limited to, polyurethanes, including polyether polyurethanes, polyester polyurethanes, polyurethaneureas, and their copolymers; polyvinylpyrrolidones; polyvinyl alcohols; polyethylene glycols and their copolymers; polypropylene glycols and their copolymers; polyoxyethylenes and their copolymers; polyacrylic acid; polyacrylamide; carboxymethyl cellulose; cellulose and its derivatives; dextrans and other polysaccharides; starches; guar; xantham and other gums and thickeners; collagen; gelatins; and other biological polymers. Preferred hydrophilic polymers are polyurethanes and polyurethane copolymers, such as polyether polyurethaneurea.

Examples of hydrophobic polymers best suited for use in the present invention include, but are not limited to, polytetrafluoroethylene, polyvinyl chloride (PVC), polyvinylacetate, poly(ethylene terephthalate), silicone, polyesters, polyamides, polyureas, styrene-block copolymers, polymethyl methacrylate, acrylic-butadiene-styrene copolymers, polyethylene, polystyrene, polypropylene, natural and synthetic rubbers, acrylonitrile rubber, and mixtures and copolymers of any of the above.

The chelates of the present invention comprises one or more oligodynamic metal oxides. In the discussion of the process below the metal oxide is silver oxide, but copper, tin, aluminum, zinc, and titanium all form metal oxides that can be chelated. Oligodynamic metal oxides useful in the present invention include, but are not limited to, silver, platinum, gold, zinc, copper, cerium, gallium, osmium, and the like. For purposes of the present disclosure, the preferred oligodynamic metal is silver.

Chelation of other metals may be employed to form the chelate. Salts may act as partial chelating agents and contain cationic ions that include, but are not limited to, calcium, sodium, lithium, aluminum, magnesium, potassium, manganese, and the like, and may also include oligodynamic metal cations such as copper, zinc, and the like. These salts contain anions that include, but are not limited to, acetates, ascorbates, benzoates, bitartrates; bromides, carbonates, chlorides, citrates, folates, gluconates, iodates, iodides, lactates, laurates, oxalates, palmitates, perborates, phenosulfonates, phosphates, propionates, salicylates, stearates, succinates, sulfadiazines, sulfates, sulfides, sulfonates, tartrates, thiocyanates, thioglycolates, thiosulfates, and the like. The invention may also be practiced with oxides serving to form the chelates including, but not limited to, oxides of calcium, sodium, lithium, aluminum, magnesium, potassium, manganese, and the like, and may also include oxides of oligodynamic metals such as silver, copper, zinc, titanium and the like.

The compositions of the present disclosure can also contain any combination of additional medicinal compounds. Such medicinal compounds include, but are not limited to, antimicrobials, antibiotics, antifungal agents, antiviral agents, antithrombogenic agents, anesthetics, anti-inflammatory agents, analgesics, anticancer agents, vasodilation substances, wound healing agents, angiogenic agents, angiostatic agents, immune boosting agents, growth factors, and other biological agents. Suitable antimicrobial agents include, but are not limited to, biguanide compounds, such as chlorhexidine and its salts; triclosan; penicillins; tetracyclines; aminoglycosides, such as gentamicin and Tobramycin™; polymyxins; rifampicins; bacitracins; erythromycins; vancomycins; neomycins; chloramphenicols; miconazole; quinolones, such as oxolinic acid, norfloxacin, nalidixic acid, pefloxacin, enoxacin, and ciprofloxacin; sulfonamides; nonoxynol 9; fusidic acid; cephalosporins; and combinations of such compounds and similar compounds. The additional antimicrobial compounds provide for enhanced antimicrobial activity.

The polymer compound and compositions can also contain auxiliary components. Examples of such auxiliary components include, but are not limited to, viscosity and flow control agents, antioxidants, conventional color pigments, air release agents or defoamers, and discolorants. The composition may also contain conventional dyes and pigments to impart color or radiopacity to enhance the aesthetic appearance of the compositions. The azodyes, in particular, have been added to the polyol chelated metal oxide complex carriers together with the polymer host to provide enhanced colored appearance of articles of manufacture including mouthguards and mouthpieces.

The compositions can also contain additional lubricating agents and other additives that enhance patient comfort and tissue health. As previously mentioned, it is also possible to add any flavorant or flavoring to the polyol carrier prior, during, or after addition of the chelated metal oxide complex. These flavoring can be man-made (synthetic) or naturally occurring flavorants.

While not wishing to be bound by the following mechanism, it is believed that many of the advantageous properties of the present compositions result from the differences in the solubility of the different chelated metal oxides present in the polyol suspension. These differing solubilities of the metal oxides in the polyol are key in determining concentration levels and resulting precipitation as well as providing varying release kinetics for the active oligodynamic metal(s). For example, with a medical device composed of, or coated with, the compositions of the present invention, those chelates that have high water solubility will be released rather quickly, providing a high initial dose of antimicrobial activity to kill bacteria introduced upon insertion of the device in the patient. This initial dose is sometimes referred to as "quick kill," and this antimicrobial activity is identified by the ability of a device or composition to create zones of no bacterial growth around the device or composition when it is placed in a bacterial culture. This test is known as a "zone of inhibition" assay. Those chelates having lower polyol solubilities will be released more quickly from the hydrophilic composition, resulting in a sustained or extended antimicrobial activity over time.

Selection of chelated metal oxides having varying degrees of solubility in the composition allows tailoring of the composition to the specific application of the article of manufacture made from the composition. Specifically, compositions of the invention can be tailored to kill bacteria introduced during the insertion of a medical device, both on the surface of the device and in the surrounding fluid and tissue, by both the quick release of antimicrobial metal oxides, followed by prolonged inhibition of bacterial migration and growth by the slower release of less soluble antimicrobial metal salts over an extended period of time. The ability to tailor the release of the oligodynamic agent is advantageous over conventional antimicrobial compositions, as it provides for both immediate and sustained antimicrobial activity.

Another advantage of the compositions of the present invention is that the formation of chelates suspended in polyols within the polymer composition produces ultra-fine particles that possess a minimal particle size for the metal oxides. The original size of the silver oxide particles are in the order of 10 nm. This minimal particle size retards settling and agglomeration. The use of suspended chelates in the composition also permits incorporation of higher quantities of antimicrobial metal oxides without the difficulties associated with other related art.

By reducing or eliminating the problems associated with conventional antimicrobial polymer compositions, the present invention provides reproducible compositions having a specific antimicrobial chelated metal oxide concentration with a specific antimicrobial ion release profile that can be tailored through the specific combinations selected to provide optimum antibiotic activity over an extended period of time. For example, compositions of the present disclosure can be tailored to release the bulk of their oligodynamic agents within 5 days for a medical device with a short term use in the body, such as for a wound dressing, or within 30 days for a device with a longer term use such as a catheter. By changing the initial relatively high concentration of the chelated metal oxide in the polyol, the final polymeric composition of matter can be tailored to a specific concentration of metal oxide. The initial release and the duration of release of the oligodynamic agents from the composition depends upon several factors. These factors include the relative solubilities of the particular chelates formed in the suspension, the concentration of the metal oxides in the suspension (carrier), and at least the phase (liquid, solid or gas), density, and chemistry of the host material. This release can range, for example, from a few days to several months, and can be tailored through the choice and number of metal oxide chelates formed in the composition for the intended purpose of the article to be manufactured.

To more completely define what is meant by polyols, the following explanation applies throughout the present specification and claims. Namely, sugar alcohols, a class of polyols, are commonly added to foods because of their lower calorific content than sugars; however, they are also, in general, less sweet, and are often combined with high-intensity sweeteners. They are also added to chewing gum because they are not broken down by bacteria in the mouth or metabolized to acids, and thus do not contribute to tooth decay. Maltitol, sorbitol, xylitol and isomalt are some of the more common types. Sugar alcohols may be formed under mild reducing conditions from their analogue sugars. These polyols can be used to provide the dispersed suspension of chelated metal salts of the present invention.

In polymer chemistry, polyols are also known and are specific to compounds with multiple hydroxyl functional groups (which are generally available for organic reactions). A molecule with two hydroxyl groups is a diol, one with three is a triol, one with four is a tetrol and so on.

Monomeric polyols such as glycerine, pentaerythritol, ethylene glycol, and sucrose often serve as the starting point for polymeric polyols. These materials are often referred to as the "initiators" and can be reacted with propylene oxide or ethylene oxide to produce polymeric polyols including polyethylene glycol. However, they should not be confused with free radical "initiators" used to promote other polymerization reactions. The functional group used as the starting point for a polymeric polyol need not be a hydroxyl group; there are a number of important polyols which are suitable for providing amine functionality. A primary amino group (—NH2) often functions as the starting point for two polymeric chains, especially in the case of polyether polyols.

Polymeric polyols are often used to produce other polymers. They can be reacted with isocyanates to make polyurethanes used to make mattresses, foam insulation for appliances (refrigerators and freezers), home and automotive seats, elastomeric shoe soles, fibers (e.g. Spandex), and adhesives.

Polymeric polyols are usually polyethers or polyesters. Polyether polyols are made by reacting epoxides like ethylene oxide or propylene oxide with the multifunctional initiator in the presence of a catalyst, often a strong base such as potassium hydroxide or a double metal cyanide catalyst such as zinc hexacyanocobaltate-t-butanol complex. Common polyether diols are polyethylene glycol, polypropylene glycol, and poly(tetramethylene ether) glycol. The examples shown below are fairly low molecular weight triols based on glycerine (a triol). Polyether polyols account for about 90% of the polymeric polyols used industrially; the balance are polyester polyols. Examples of these structures are shown below;

Another class of polymeric polyols are the polyesters. Polyesters are formed by condensation or step-growth polymerization of diols and dicarboxylic acids (or their derivatives), for example diethylene glycol reacting with phthalic acid. Alternatively, the hydroxyl group and the carboxylic acid (or their derivatives) may be within the same molecule, as in the case of caprolactone. The example below is an idealized structure that could be obtained by reacting pentaerythritol (a tetrol) with gamma-butyrolactone.

Hydroxyl-terminated polybutadiene is a polyol used to produce polyurethane. Polyester polyols from vegetable oils, known as natural oil polyols or NOPs, are replacing some epoxide-based polyols and can also be used for making the dispersed metal oxide suspension "carrier" of the present invention.

All of the various forms and types of polyols listed above may be used for dispersing the chelated metal oxides and/or helping to form the final polymeric composition containing a homogeneously dispersed chelated metal oxide substance (carrier) throughout the final polymeric composition (host). In the case of introducing silver oxide into polyols, it may be necessary, in order to provide higher concentrations of the silver oxide to first suspend the chelated silver oxide in glycerine and then incorporate the infused glycerine into the polyol. This technique works well for glycerine in lower molecular weight PEGs (100-700 MW).

In one disclosed embodiment, the present disclosure comprises one or more chelated silver oxide forms as the oligodynamic agent which is combined with a liquid phase polyol or glycerine, producing a homogenous dispersed suspension of the chelated silver oxide. In another embodiment, the composition optionally contains additional chelated metal salts of other oligodynamic metals, such as zinc, gold, copper, cerium and the like. In still another embodiment, the composition optionally comprises additional chelated salts of platinum group metals such as platinum, palladium, rhodium, iridium, ruthenium, osmium, and the like. The compositions optionally contain any other components that provide beneficial properties to the composition or improve the antimicrobial effectiveness of the composition.

In a second aspect, the present invention relates to a process for producing these antimicrobial compositions. The process comprises the formation of chelates of oligodynamic agents in solutions, dispersions, or combinations of polymers solutions and dispersions. The terms "polymer composition" and "polymer solution" are used interchangeably throughout the specification and claims and both are interpreted to be understood as any polymer solution, dispersion; or combination of polymer solutions and dispersions including but not limited to solid state compositions. The chelated metal oxide suspension (a carrier in some cases) is formed first and then can be subsequently added to the polymer (the host) to form another (new) composition or the chelated metal oxide complex can be formed in situ in the polymer composition.

One preferred embodiment is for the chelated metal oxide to be a silver oxide that is dispersed in glycerine prior to compounding with the polymer and optionally with colorant that is known to provide color without interfering with the processibility, color desired, or physio-chemical behavior of the final compound. The final compound developed for subsequent processing of the article, can therefore be either a one, two, or at least three component system; a chelated metal oxide suspension, the metal oxide suspension added to the polymer, and the metal oxide, polymer composition, and optionally incorporation of a colorant. Four or more component systems would include the additional incorporation of both organic and inorganic fillers such as antioxidants, other anti-bacterial compositions, flavorings, flame retardants, etc., which would impart special additional properties and benefits.

It has also been found that the addition of the metal oxides in polymeric systems results in the ability of the polymeric systems to become conductive or at least semi-conductive especially for membrane and wire and cable application. Additionally, the chelated metal oxides that are compounded into the base thermoplastics will provide reduced or selective gas permeability especially for separating or filtering mono and diatomic gases such as nitrogen, oxygen, argon, etc. Another area where the chelated metal oxides are of great benefit are for UV resistance. Although normally associated with zinc oxide, chelated silver oxide also exhibits UV resistance. Use of chelated copper, nickel, tin, and aluminum oxides may provide better economic benefits for some of the products that can be formed from these compounds. These associated properties for the two or more component compound systems are also part of the present disclosure.

In most, if not all cases, the polymer physio-chemical, physical, and/or mechanical properties without the chelated metal oxides are either not compromised or not substantially compromised in comparison with the identical polymer system that does not have the chelated metal oxides compounded into the system from the metal oxide complex (carrier system). This is also a very important and distinguishable characteristic of the present invention. In terms of commercial value, the fact that unique properties can be incorporated into polymer systems with relatively minor added costs based on very low concentrations (normally less than 300 ppm) of the metal oxide, provides a very distinct advantage over any known polymer additive technology, especially for the incorporation of silver oxides.

Articles of manufacture for the compounds of the present disclosure (chelated metal oxides formed within polymer) include almost too many to list. The list given below is not intended to be all inclusive, but has been separated based on desirable parametric attributes.

For antibacterial, antimicrobial, antiviral, anti-fungal and anti-mold products, the desired articles of manufacture include at least the following;

Medical devices and hospital products including tubing, masks, mats, plastic cups, surgical instruments, etc., which also include, but are not limited to, catheters, cannulae, stents, guide wires, implant devices, contact lenses, IUDs, peristaltic pump chambers, endotracheal tubes, gastroenteric feeding tubes, arteriovenous shunts, condoms, oxygenator and kidney membranes, gloves, pacemaker leads, wound dressings, as well as breathing masks and essentially any product that comes into contact with the skin or provides a mechanism for filtering gases of liquids inhaled or ingested by humans. The need for reducing or eliminating "staph infections" in the medical community is well known and the compounds of the present invention have been proven to provide these properties without sacrificing other physio-chemical attributes. This is in part due to the nature of adding relatively low (ppm) concentrations of the chelated metal oxides.

Children's items, including toys, bottles, pacifiers, and essentially any article of manufacture made for infants or children also benefit greatly from the use of the compounds of the present disclosure.

Kitchen appliances, countertops, cutting boards, and generally anywhere food is prepared, stored or served for eating by humans or animals, are also articles of manufacture included in the present disclosure. This includes incorporation of the food edible glycerine based chelated silver oxide into any liquid or solid food substance. The chelated silver oxide is not only GRAS (generally accepted as safe) but is also non-toxic and meets any FDA requirements, so that it can be used with glycerine to establish many novel and unique items for animal and human ingestion (solid foods, liquid foods, and drinks including water and ice).

Other home products include bathroom accessories such as bathroom fixtures, flooring, cleaning products, air filtration items, food storage items HVAC, luggage and office and school products. Toilet seats and portable toilets (including those for aircraft and automotive use) are areas associated with high level of bacteria that would also benefit from the technology described herein. Shower curtains as well as toothbrushes are further articles of manufacture sold in high volume throughout the world and touched or used by individuals on a routine basis.

The chelated metal oxide in polyols are suitable (both with and without compounding with the polymer systems) for use in paints, personal care products, pool and spa products, grout and sealants as well as for adhesives and generally anywhere inside or outside the home or industrial/commercial buildings where mold and/or mildew is a source of concern.

Sporting equipment such as mouthguards, mouthpieces, and in general, dental appliances have been and continue to be a big thrust for the use of the present composition of matter. The use of chelated silver oxide as a substance which can be ingested (as opposed to other forms which are in carriers that are inappropriate for injection—such as clay nano-particles and other solid forms of the silver oxides) provide opportunities for applications of products designed to be ingested or used with already FDA approved plastics and subsequent articles of manufacture for human exposure. The chelated metal oxide composition in a vegetable based glycerine base is useful for essentially any food products and could even be combined with water in any form—including ice—such that the food and water (or any water based substance) will exhibit antimicrobial/antibacterial and anti-viral properties. Certainly there is ubiquity involved regarding the many food, food preparation and fluid consumption applications (including beverages) for just the glycerine based complex which can be added to essentially all food and beverage items (including all known baked goods) as it is non-toxic, "green" and sustainable and food-grade ingestible. "Green", in this sense refers to a large number of products now being touted as either organic and/or non-toxic and/or earth grown or earth derived substances that will not cause toxic waste when manufactured, used, and/or disposed. The concept of "cradle to cradle" or "cradle to grave" for products using Life Cycle Assessment tools to determine the validity of the term "green" is, in part, a methodology with which the inventors have experience and is useful in further defining "green" products.

In addition, the same glycerine based chelated silver oxide complex can be added directly to flavorings and flavored items. In some cases, this could include flavored polymeric substances that are treated with the chelated silver oxide carrier.

Vacuum cleaners, water filters and storage devices, aircraft interiors including serving trays and air exchange ducts. In commercial aircraft the propensity to high levels of bacterial exposure has been and continues to be of large concern to the industry. Baby changing stations, cleaning supplies, commercial high chairs, dispensers, door hardware (including knobs), electronics, elevators, storage units, surface coatings, and transportation products of all types will also benefit from the technology described herein. Yoga and wrestling mats and mattresses as well as wrestling mats are also articles of manufacture covered by the present disclosure.

For automobile interiors there are numerous applications for articles of manufacture including steering wheels and covers, window handles and buttons, dashboards, radio and navigation controls, etc.

All forms of communications devices including cell phones and all the peripheral equipment regarding such, personal computers, mobile devices, tablet devices (ipads, etc.), are all articles of manufacture that will benefit from the antibacterial properties assured by using chelated silver oxide fortified polymer systems as described herein.

Antibacterial and UV resistant window coverings are also desirable articles of manufacture. Footwear, medical textiles, and protective wear, are additional articles of manufacture where the chelated metal oxide complexes and compounds of the present disclosure can also be utilized.

In another aspect, the present invention relates to an article of manufacture which comprises a substrate and the antimicrobial compositions of the present invention. In a disclosed embodiment, the composition is employed in the manufacture of the article itself. Thus, the final article is composed of one or more of the compositions of the present invention, alone or in admixture or by direct injection during processing with other polymeric components. A preferred embodiment is to manufacture the compound by compounding, via heat and/or pressure, a thermoplastic with the chelated silver oxide prepared as described below.

Optionally, additional components can be added to the antimicrobial compositions of the present invention. These components include, but are not limited to, additional oligodynamic agents, additional soluble salts, and any other components which provide the compositions with beneficial properties or enhance the antimicrobial activity of the compositions without interfering with the basic polymeric properties. Such components include, but are not limited to, antimicrobial agents, antibiotics, and other medicinal agents.

DESCRIPTION OF THE INVENTION

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases.

The term "safe and effective amount," as used herein, means an amount of an applied compound, component, composition or complex to significantly induce a positive antibacterial/microbial/viral benefit to the user providing a reasonable benefit to risk ratio, within the scope of sound medical judgment.

All percentages and ratios used herein are by weight of the total composition and all measurements made are at 25 degrees Centigrade unless otherwise designated. Unless otherwise indicated, all percentages, ratios, and levels of ingredients referred to herein are based on the actual amount of the ingredient, and do not include solvents, fillers, or other materials which may be combined with the ingredient in commercially available products.

Described is an initial liquid composition with at least antimicrobial, antibacterial, and/or anti-viral properties comprising chelated metal oxide particles suspended in a polyol, such that metal oxide particles are homogeneously dispersed in the primarily liquid based polyol carrier and such that the chelated metal oxide particles form a stable complex suspension that can eventually become an alkaline based aqueous silver oxide dispersion. The suspension can be optionally further complexed with a combination of chitosan where the resulting metal oxide complex is provided in a concentration of between 0.1 and 25 weight percent. The liquid composition can be subsequently added to essentially any polymer or polymer compound/system where the polymer degrades or melts at a temperature lower than the polyol carrier degradation temperature. The metal oxide complex may also impart beneficial semi-conductive or conductive as well as permeability and flammability property changes to the polymer (host) system. This technique allows for providing chelated metal oxide complexes to essentially any polymeric host without substantially altering the necessary physio-chemical properties of the original polymeric system absent the polyol chelated metal oxide complex additive carrier infused into the same polymeric host.

The total amount of chelated silver oxide complex suspension formed in the polyol ("carrier") and eventually captured within the polymeric compound forming the antibacterial formulation (host) of the present invention may be varied within wide parameters, but should be in a sufficient amount for the composition to act as a germ-like barrier and provide a polymeric compound that effectively inhibits, reduces and essentially eliminates bacterial growth. The same holds true for imparting other properties including reducing permeability (particularly to oxygen), flammability, and increasing UV resistance.

Generally, in one embodiment, the anti-bacterial, antimicrobial, germ barrier effective amount of the chelated metal oxide in the polyol is generally in the range of 0.001 to 10 weight percent based on the total weight of the polyol formulation so that one can add smaller amounts and concentrations of the polyol carrier into the polymer resin to form the resultant polymeric composition and the remaining amount would be the antimicrobial effective amount of the silver oxide complex.

In another embodiment, the antimicrobial composition comprises at least one either aqueous or glycerine phase formulated, for example, in a form chosen from water-in-oil emulsions, oil-in-water emulsions, and multiple emulsions, e.g., oil-in-water-in-oil and water-in-oil-in-water triple emulsions.

In another embodiment, the at least one phase comprises polyol and generally other polyol soluble or miscible solvents. The solvents may be chosen from short-chain monoalcohols, for example, monoalcohols of C1-C4, such as ethanol and isopropanol; and diols and polyols themselves, for example, ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether and sorbitol.

In yet another embodiment, the carrier vehicle comprises propylene ethylene glycol and/or glycerol. An especially useful component for preparing the antibacterial portion of the formulation is the use of propanediol.

In a further embodiment, the composition comprises at least one water-immiscible organic liquid phase. The at least one water-immiscible organic phase generally comprises at least one hydrophobic compound that renders the phase water-immiscible. The at least one water-immiscible organic phase is liquid (in the absence of a structuring agent) at room temperature (20 to 25 degrees Centigrade).

In yet another embodiment, the at least one water-immiscible organic liquid phase is chosen to be the carrier for the chelated silver oxide and can be from an oil and/or a mixture of oils and comprising at least 80% of compounds with a vapor pressure not exceeding 4 kPa (30 mmHg) at 25 degrees Centigrade. The at least one water-immiscible organic liquid phase, for example, comprises at least one emollient oil chosen from volatile and non-volatile, silicone-based, and hydrocarbon-based emollient oils. These emollient oils are, for example, described in U.S. Pat. Nos. 4,822,596 and 4,904,463, hereby incorporated by reference.

As used herein, volatile silicones are defined, in a known manner, as being compounds that are volatile at room temperature. Mention may be made, for example, among these compounds, to cyclic and linear volatile silicones of the dimethylsiloxane type, whose chains comprise from 3 to 9 silicone-based residues. As used herein, non-volatile silicones are defined, in a known manner, as being compounds with a low vapor pressure at room temperature, such as polyalkylsiloxanes, such as linear polyalkylsiloxanes, including linear polydimethylsiloxanes, or dimethicones; polyalkylarylsiloxanes, for example, polymethylphenylsiloxanes; and copolymers of polyether and siloxane, for example, dimethicone copolyols. Among the non-volatile emollient oils that may be used, examples include hydrocarbon-based derivatives, mineral oils, fatty alcohols, esters of C3-C18 alcohols with C3-C18 acids, esters of benzoic acid with C12-C18 alcohols and mixtures thereof, C2-C2-C6 polyols, for example, chosen from glycerol, propylene glycol or sorbitol, polyalkylene glycol polymers.

Mixtures of carrier materials and/or surfactants are also usable as carriers for the chelated metal oxides. The total amount of carrier material employed is for some embodiments, from 1% to 99%, and for other embodiments, from 60% to 98%, expressed as a weight percentage of the total weight of the composition. The chelated metal oxide complex is normally added in amounts up to 2.5 to 10 percent by weight for most polymer systems. For food and beverage the percentages are usually smaller.

In a separate embodiment, the antimicrobial compositions further include at least one other agent that imparts color or other aesthetics to the composition, including organic structurants that are non-polymeric or polymeric. Examples of non-polymeric structurants include, but are not limited to, colorants or dyes.

The antimicrobial chelated metal oxide component dispersed suspension can be dispersed in one or more of a selected group consisting of polyvinyl alcohols, polyvinyl pyrrolidone, polyalkylene oxides, celluloses, cellulose derivatives, polysaccharides, polysaccharide derivatives, polycarboxylic acids, salts of polycarboxylic acids, polyamino acids, peptides, polyamides, polyacrylamides, polyesters, poly(vinyl methyl ether-co-maleic anhydride), alginates, alginate derivatives, pectins, polyethylene oxides, gelatins, carrageenans, chitosans, starches, starch derivatives, and combinations thereof. In all cases, these "carriers" must be in the liquid phase at room temperature or ambient conditions and capable of keeping the chelated metal complex in a stabile state so that blending, combining and/or compounding the dispersed chelated metal suspension into a polymer matrix does not reduce or eliminate the antibacterial effects in the final polymeric composition used to manufacture the desired article.

The composition of the invention also can comprise other components that may be chosen depending on the carrier and/or the intended use of the formulation in the host. The optional components are used in an amount that does not substantially or adversely impact the desired anti-bacterial effect.

In addition to the preservative nature of the chelated metal oxide complex, another embodiment includes the use of at least one preservative compound in combination with the topical anti-chafing chelated silver oxide compositional material. The preservative compounds may be present in an amount of 0.5% to about 3% by weight of the formulation. Desirably, the preservative compound is effective against yeast, particularly *Candida albicans*; molds, particularly *Aspergillus niger*; and bacteria, particularly *S. aureus, E. coli*, and *E. cloacae*. Examples include disodium ethylene diamine tetraacetic acid, methylparaben, and diazolidinyl urea. The chelated silver oxide complex also serves as a chelating agent to block the activity of bacterial ureases, lipases, proteases, and decarboxylases produced by *Klebsiella pneumoniae, Proteus mirabilis*, and *E. coli* bacteria In addition the chelated silver oxide can act as a preservative for pharmaceutical, antibiotic, and other medications.

In one other embodiment, the antibacterial polyol based metal oxide liquid complex suspension and final polymeric composition may also include fragrances. Examples include but are not limited to citrus, floral, spicy, lavender, woody, mossy, oriental, herbal, leather-tobacco, and aldehydic groups. Typically, fragrance materials are supplied as concentrates, which generally contain up to about 3 percent fragrance by weight. Examples include natural products such as essential oils, flower oils, natural extracts from resins, gums, balsams, beans, mosses and other plants, and animal products such as ambergris and musk, as well as synthetic aromatic materials.

Process for Preparing the Composition and Documented Results

In a first aspect, the present invention relates to a process for producing the compositions of the invention. In general terms, the process comprises the formation of suspended chelates of oligodynamic agents first prepared in polyols and subsequently added into polymer compounds via mixing/blending/compounding using pressure and/or heat. The chelated metal oxide suspension is normally formed first and then added to the polymer composition or can be formed in situ in the polymer composition.

This results in a polyol (glycerine) based chelated silver oxide complex suspension that is a liquid at room temperature. This method requires following a procedure such as described below in Example 1.

Example 1

The process of forming the chelated silver oxide is best described in Working Example 1 as follows;

On a 500 gram basis to make a 4000 ppm concentration of a chelated silver oxide suspended in a glycerine base, all materials are weighed out in advance of mixing;

1. Take 0.47 wt. % (2.35) grams silver oxide powder (nominal size is 10 nm) and blend at high speed (at least 1000 rpm) into 31.54 wt. % (157.7) grams distilled water at 180 degrees Fahrenheit (82 Centigrade) for up to 3 minutes. The pH of this slurry should rise to 8.21. More than 3 minutes will cause too much oxidation. Put this dark slurry solution aside.
2. Take 5.65 wt. % (28.25 grams) of citric acid and introduce this into 5.65% (28.25) grams of distilled water at 82 degrees Centigrade and mix for 3-4 minutes. The pH of this solution should level out at 1.83. Put this solution aside as well.
3. Take the slurry of (1) above and add to the solution of (2) above and keep the mixture at 82 degrees Centigrade under rapid agitation and continue mixing in the slurry at high speeds (again 1000 rpm or greater) for 3-4 minutes. It is important that this order of addition be used or the chelation will be incomplete or may not occur at all. The chelation reaction is extremely rapid (within less than 3 minutes after full addition of (1) to (2). It appears the reaction is endothermic as the chelation reaction will not reach completion at room temperature. The temperature is at 82 degrees Centigrade and the reaction appears complete within a few minutes (no evidence of silver powder remains in the solution)
4. Introduce (3) above into 56.18 weight percent of glycerine (USDA kosher grade vegetable is best choice to ensure no toxicity and full ingestibility)—43.82 weight percent of (3) above, also at 82 degrees Centigrade, with moderate agitation (at least 500 rpm) for 2-3 minutes and allow to cool to room temperature. It is possible to neutralize the pH to 7 or above at this stage using, preferably sodium carbonate. Arginine and other amino acids seem to bind with the chelated oxide complex and cause normally undesirable enlargement of silver oxide particles so that there will be eventual precipitate formation.
5. At this point the 500 gm. chelated silver oxide glycerine based complex suspension (acting as a carrier) is homogeneous, stabile, and ready for use. Concentrations of this silver oxide complex are stabile (no precipitate), using this 4 step method, to at least 4000 ppm. Forming the precipitate leads to other complex formations of the silver oxide suspension and it is not known if the precipitate is as effective in providing the same effectiveness or stability in terms of the antibacterial, antiviral, antimicrobial, or even if the UV, conductivity, and/or permeability/flammability properties are constant and reproducible.

In this specific example, the incorporation of 4000 ppm of chelated silver oxide is suspended in a glycerine solution. Use of other polyols, such as PEG, have also been successfully employed but often using glycerine with higher concentrations of AgO as the initial carrier that is subsequently added to the PEG. Once the glycerine-based complex suspension was formed and stabilized, in this case with a 4000 ppm chelated silver oxide concentration, it was possible to successfully incorporate (via thermal processing) this liquid suspension into EVA (ethylene vinyl acetate—Elvax® 260) using 2.5 weight percent of the glycerine complex in 97.5 weight percent of the EVA.

This compounding was accomplished using a Braebender extruder by heat processing the Elvax® 260 (a DuPont Trademarked polymer resin) at 140 degrees Fahrenheit before addition of the chelated silver oxide glycerine complex in an amount of between 0.01 and 5 weight percent of the complex to the base EVA polymer. At 5 weight percent of the liquid suspension, the compounding was unsuccessful in that the mixture became "gooey" and would not flow out of the extruder properly. At 2.5 weight percent, using a 4000 ppm concentration, no such operational issues occurred, and it was possible to develop a compounded polymer system with the chelated silver oxide complex that produced a final concentration of 100 ppm of the silver oxide in the EVA.

This 2.5 weight percent silver oxide complex additive to the EVA polymer was sufficient to provide 100 ppm of the chelated silver oxide and yielded the antibacterial properties shown in Table 1 below;

TABLE 1

Colony Forming Units (CFU) Collected After Treated and Untreated Mouthpieces Molded from Ethylene Vinyl Acetate Exposed to P. aureginosa and S. aureus Results for Silver Oxide Complex in Glycerine Complex (initial concentration 4000 ppm, final concentration 100 ppm in the Mouthpiece)

| | | Contact Time "0 Hours" | | Contact Time - "24 Hours" | | Percent Reduction | |
|---|---|---|---|---|---|---|---|
| Sample ID | | P. aeuruginosa CFU/ml. | S. aureus CFU/ml. | P. aeuruginosa CFU/ml. | S. aureus CFU/ml. | P. aeuruginosa | S. aureus |
| #A (blank) | | | | | | | |
| | AVG | 5,300,000 | 5,400,000 | 10,200,000,000 | 1,566,666 | NR | 73% |
| | GM | | | 9,804,468,321 | 1,442,249 | | |
| # B | AVG | NR | NR | 227,000,000 | 493,000 | 98% | 91% |
| | GM | NR | NR | 226,709,078 | 488,595 | | |

TABLE 1-continued

Colony Forming Units (CFU) Collected After Treated and
Untreated Mouthpieces Molded from Ethylene Vinyl Acetate
Exposed to *P. aureginosa* and *S. aureus* Results for Silver Oxide
Complex in Glycerine Complex (initial concentration 4000 ppm,
final concentration 100 ppm in the Mouthpiece)

| Sample ID | | Contact Time "0 Hours" | | Contact Time - "24 Hours" | | Percent Reduction | |
|---|---|---|---|---|---|---|---|
| | | *P. aeuruginosa* CFU/ml. | *S. aureus* CFU/ml. | *P. aeuruginosa* CFU/ml. | *S. aureus* CFU/ml. | *P. aeuruginosa* | *S. aureus* |
| # C | AVG | NR | | 241,000,000 | 460,000 | 98% | 91% |
| | GM | NR | | 240,163,742 | 451,991 | | |

AVG = Average of three triplicate values
GM = Geometric Mean of the three triplicate values (used to calculate % reduction)
NR—No Reduction The data above was provided from an Independent test laboratory (EMSL located at 1800 Water Place, Ste. 2287, Atlanta, Ga. 30339) using the ASTM E2180 test procedure—"Standard Method for Determining the Activity of Incorporated Antimicrobial Agent(s) in Polymeric or Hydrophobic Material".

Three molded samples incorporating the chelated silver oxide complex into Elvax® 260 (tradename by DuPont for etheylenw vinyl acetate) were tested as follows for Samples A, B and C;

Sample (A)=Elvax® 260 Blank Mouthpiece
Sample (B)=Elvax® 260 with 2.5% glycerine AgO complex Mouthpiece
Sample (C)=Elvax® 260 with 2.5% glycerine AgO complex and 0.05 weight percent blue pigment dye—Phthalocyanine Blue—CAS number 147-14-8 (Sunfast Blue—recommended 15:1 let down ratio) Mouthpiece The three samples were received to evaluate the effectiveness of the agents incorporated or bound into the mainly flat (2-D) hydrophobic or polymeric surfaces. The test organisms utilized were *Staphylococcus aureus* (ATCC 6538) and *Pseudomonas aeruginosa* (ATCC 15442). Two separate agar slurries were prepared, one for each organism. The agar slurries vcontined 1 mL of the test organism (concentration=$5\times10^8$ cells/mL), 0.85 g NCl, 0.3 g agar, and 100 mL of deionized water. The final inoculum concentration was equal to about $5.0\times10^6$ cells/mL.

All of the samples were prepared in triplicate and aseptically cut into equally sized pieces (4 pieces for each treatment, about 6.29 cm$^2$). One portion of 0.70 mL of each agar slurry was applied to the prepared samples. Using both sonication and manual vortexing the agar slurry was removed after gelling from one set of control samples and plate counts were performed. The data recovered was designated '0' hours.

The remaining set of control samples and the treated material was incubated at 35 degrees Centigrade for 24+/− hours with the solidified agar slurry intact. The agar slurry was again removed and processed with sonication and vortexing. Plate counts were performed. The data retrieved from this set of samples was designated '24 hours'.

Calculation of 'percent reduction' was done by comparing the geometric mean of each time point data set with that of the relevant time point control.

In theory, it should be possible to infuse the glycerine based chelated silver oxide complex suspension In any polymer that is melt processable up to 290 degrees Centigrade as 290 C is the boiling point for glycerine. In practice, however, the TGA (standard thermal gravimetric analysis) plot shown in FIG. 1, indicated that above 250 degrees Centigrade there is significant (greater than 20 wt. %) loss due tothermal degradation. This is one of the reasons that higher boiling carriers (such as higher molecular weight polyethylene glycols) may be employed for infusion of the silver oxide into higher melting polymer systems. PEG's should also allow for incorporation of higher concentrations of the chelated metal oxide, thus also allowing for final higher concentrations of the metal oxides to be infused into the polymer host. This may be necessary to impart better anti-bacterial properties or reduce permeability, increase resistance to UV, reduce flammability, or impart some combination of these desirable attributes into the polymer host. The result is that the articles of manufacture derived from this enhanced polymer host can be tailored for the final properties desired.

Keeping the metal oxide chelate complex suspended without precipitation (for an indefinite time period—at least many months and up to years) is known to impart the antibacterial properties as given below in Table 2:

TABLE 2

Anti-Bacterial Paint Results for Chelated Silver Oxide
in PEG Suspension Complex (initial concentration 2000
ppm, final concentration 100 ppm in the paint)

| Organism | Initial Organism Count in Cultured Suspension Before Exposure to PEG Complex | Final Organism Count After Exposure to PEG Complex |
|---|---|---|
| *P. aeruginosa* | $1.0 \times 10^5$ | 25 CFU |
| *S. aureus* | $7.0 \times 10^5$ | 412 CFU |
| *E. coli* | $6.8 \times 10^5$ | 12 CFU |
| *C. albicans* | $1.0 \times 10^5$ | 199 CFU |
| *A. niger* | $1.0 \times 10^5$ | 8 CFU |

The results in Table 2 are from the addition of the chelated silver oxide complex at 2000 ppm in a PEG (polyethylene glycol) base that is subsequently added to an interior acrylic semi-gloss paint (product code 240100) in a let-down ratio of 20:1. The final concentration of the silver oxide chelate complex in PEG was 100 ppm. The paint was then tested to determine the antimicrobial and antibacterial properties as follows;

Using a 9×13 glass dish that was coated with three layers of paint; ⅕ of the area was swabbed with each 105 organism suspension. The organism suspensions were allowed to dry on the surface of the dish for approximately thirty minutes. The surface of the dish was inoculated with *P. aeruginosa* (ATCC 9027), *S. aureus* (ATCC 6538), *E. coli* (ATCC 8739), *C. albicans* (ATCC 10231) and *A. niger* (ATCC 16404). Contact slides were placed on the inoculated areas. *P. aeruginosa. S. aureus*, and *E. coli* were incubated at 30-35 degrees Celsius for 72 hours and enumerated. *C. albicans* and *A. niger* were incubated at room temperature for 5 days.

Applicants have found that chelated silver oxide and polyol and/or glycerine when complexed into a polymeric compound exhibits the needed unique characteristics combining lubricity, processibility, antimicrobial (as well as semi-conductive/conductive, UV resistant, permeability and flammability changing) properties to provide polymeric compounds meeting multi-purpose criteria. The chelated silver or other metal oxide complexes, which is also biocompatible, adds antimicrobial properties into the polymers to provide at least an article of use that also reduces or eliminates contamination by bacteria, fungi, mold, germs, and microbes and in some cases, viruses. There is a body of evidence that suggests the same metal oxide complexes will provide conductive, UV resistant, permeability, and flammability changing properties for the polymers and subsequent articles of manufacture.

Other metal oxide chelates using acids other than citric acid (such as glycolic acid, nitic acid, etc.) are anticipated in the present invention. Using citric acid leads to chelated silver oxides that are ingestible (not toxic) for humans and other mammals. This chelated silver oxide described above is also safe and usable for exterior application to the skin. It is non-toxic and ingestible as well as "green" and sustainable which also is distinctive from other metal oxide compositions developed by previous investigators.

Such components include, but are not limited to, antimicrobial agents, antibiotics, and other medicinal agents. Additionally, other salts may be added to the composition that do not react in solution but provide some beneficial effect such as stabilization of the suspension, modification of chelated metal oxide ion release rate, promotion of galvanic action, increase in antimicrobial effectiveness, or enhancement of biocompatibility. Further, other compounds may be added to the composition, including, but not limited to, medicinal agents, lubricants, nutritional agents, antioxidants, dyes and pigments, and other additives.

As noted above, any polymer can be used to form the compositions of the present invention. When hydrophilic polymers are used, it is preferable that the polymers be soluble in water or in organic solvents containing some water. The ability to add water to the polymer composition without precipitating the polymer allows the addition of water-soluble salts directly to the coating composition. The use of water in the polymer composition increases the solubility of the salts, resulting in the formation of finer more stable colloids. However, it takes longer for the coating compositions to dry when the water content is very high. For this reason, the preferred amount of water in the hydrophilic polymer compositions is about 50% or less. Such concentrations provide for faster drying times while maintaining the beneficial properties provided by the water in the composition.

In contrast, when hydrophobic polymers are used either alone or in combination with hydrophilic polymers, it is desirable to limit the amount of water present in the composition to avoid precipitation of the hydrophobic polymer with the colloid. In such instances the amount of water present in the polymer composition is preferably 1% or less. Thus, when hydrophobic polymers are employed in the present invention, the preferred water content of the polymer compositions is between about 0.1% and 1% by weight. It is advantageous to employ salts that are soluble in alcohols or organic solvents when hydrophobic polymers employed.

It is also possible to prepare polymer compositions from supercritical fluids. The most common of these fluids is liquefied carbon dioxide.

Polyols useful as solute-like suspension agents for the chelated silver oxide include, but are not limited to, polyethylene glycols, polyester polyols, polyether polyols, caster oil polyols, and polyacrylate polyols, including Desmophen A450, Desmophen A365, and Desmophen A160 (available from Mobay Corporation), poly(ethylene adipates), poly(diethyleneglycol adipates), polycaprolactone diols, polycaprolactone-polyadipate copolymer diols, poly(ethyleneterephthalate)diols, polycarbonate diols, polytetramethylene ether glycol, ethylene oxide adducts of polyoxypropylene diols, and ethylene oxide adducts of polyoxypropylene triols.

The chelated silver oxide solution of the present invention can be further processed for a wide variety of dispensing methods, but for the purposes of the present disclosure a dispersion into a glycerine base is provided.

The present disclosure also relates to an antimicrobial topical composition comprising complexes of chelated metal oxides and more specifically, a version utilizing chitosan-silver oxide, and in particular to solutions comprising complexed chitosan-silver oxide bio-films, and to the methods of making the same to form a polyol based dispersion of chelated silver oxide suspensions that can be compounded or blended with polymeric substances, yielding antibacterial compounds with essentially imperceptible changes in physio-chemical properties when processed into articles of manufacture. The use of chitosan to make the chelated metal oxide complex suspension is helpful in that it imparts biofilm properties to the complex useful for application to mammalian skin.

For this embodiment, the chitosan solution is formed by first providing chitin, which is a homopolymer of beta (1-4)-linked N-acetyl-D-glucosamine. Rinsed, dried and ground chitin can then undergo a process of deacetylation to convert some N-acetyl glucosamine to glucosamine, a primary component of chitosan. The chitosan solution can then be prepared by mixing chitosan with an alpha-hydroxy acid such as glycolic acid and allowing it to thicken. A silver solution can be prepared by mixing silver oxide with a combination of a carboxylic acid and the chitosan solution (such as citric acid) to form silver oxide chelate. Since the chitosan solution is cationic, and the silver solution may be generally neutral, the resulting silver-oxide chitosan complex will be primarily cationic. The cationic solution of the present invention will bond nicely with the generally negatively charged human skin. In use, citrate helps promote uptake of the silver by bacteria.

According to one advantage of the present invention, an antimicrobial solution having high immediate and short term effectiveness is provided. This is accomplished as bacteria are attracted to the citrate in the solution. The citrate promotes uptake of the silver oxide ion in the bacteria, resulting in effective killing of the bacteria. In fact, as shown in Tables 1 and 2 above and other data obtained from independent test laboratories, the present invention comprising the chitosan-silver oxide complex has been evaluated to be effective against *salmonella, E.-coli*, MRSA (staph), *Pseudomonas aeroginosa, Serratia marcescens* and *Klebsiella pnuemoniae*.

According to another advantage of the present embodiment, an antimicrobial solution having high residual effectiveness and stability is provided. This is accomplished as the antimicrobial solution can be prepared to not only be relatively stable but also exhibit low volatility and does not readily evaporate. In part this is due to the hydration of the silver oxide powder in deionized water prior to any chelation and the fact that this causes the silver oxide powder to form a thin and eventually alkaline slurry—again prior to any chelation and before the addition of the chitosan and carboxylic acid. Using certain alkaline substances that will enlarge the chelated metal oxide particles are not appropriate In that this will cause premature precipitation.

Related and according to a further advantage of the embodiment, an antimicrobial silver oxide solution that readily bonds to a user's skin such that it remains in place is provided. This is accomplished because in this silver oxide complex suspension, the silver oxide is further bonded to the chitosan to further form a biofilm forming complex and thus forms a molecule that is positively charged or cationic. The skin of the human body typically exhibits a negative charge and accordingly is anionic. The natural electrostatic attraction of the chitosan-silver oxide complex to the surface of the skin allows the complex to bond with the skin. In fact, laboratory results have shown a 100 ppm chitosan-silver oxide complex to have a residual efficacy of greater than 24 hours under laboratory conditions. This is achieved without the use of synthetic polymers and without the utilization of alcohol, benzalkonium chloride or triclosan. The chelated silver oxide component is the active ingredient that quickly dispatches the bacteria upon contact and also provides unsurpassed biocompatibility qualities not seen for other chelated silver complexes, primarily due to the fact that the silver oxide is stabilized in an alkaline medium prior to chelation and complexing.

According to a still further advantage, an antimicrobial silver oxide alkaline based solution that is stable, portable and easily dispensable is provided. The stabilization of the silver oxide in an aqueous alkaline medium prior to further complexing provides both instant biocompatibility and antimicrobial action with most organisms at a cellular level. There is recent evidence that silver oxides actually are effective in providing cellular changes through the DNA and by chelation it is believed that the silver oxide of the present invention allows for superior intracellular activity when compared with other known liquid or solid forms of silver (or any metal) oxide—especially that of colloidal metal oxides.

Other advantages, benefits, and features of the present invention will become apparent to those skilled in the art upon reading the detailed description of the invention and studying the drawings.

BRIEF DESCRIPTION OF THE DRAWINGS

FIG. 2 is a flow chart showing a preferred embodiment of the process of making chitosan from chitin.

FIG. 3 is a flow chart showing a preferred embodiment of the process of making a chitosan solution.

FIG. 4 is a flow chart showing a preferred embodiment of the process of making a chelated silver oxide solution which could be applied to most other metal oxides.

FIG. 5 is a flow chart showing a preferred embodiment of the process of preparing the polyol based chelated metal oxide complex of the present invention.

Figure 1:
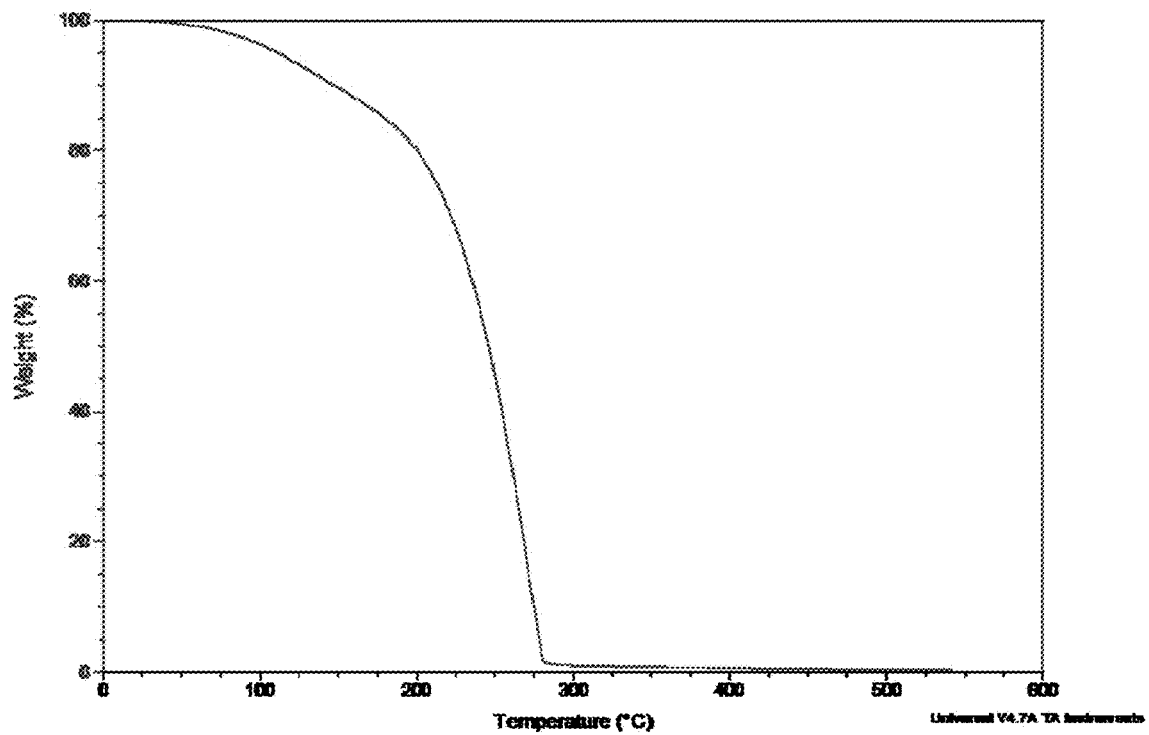
FIG. 1 is a TGA Plot for Chelated Silver Oxide in Glycerine at 4000 ppm AgO

While the invention will be described in connection with one or more preferred embodiments, it will be understood that it is not intended to limit the invention to those embodiments. On the contrary, it is intended to cover all alternatives, modifications and equivalents as may be included within the spirit and scope of the invention as defined by the appended claims.

Looking now to FIG. 2, a process 10 of forming chitosan is provided. Raw material is provided in step 11. The raw material is chitin. Chitin is a homopolymer of beta (1-4)-linked N-acetyl-D-glucosamine. Chitin is an abundant naturally occurring and renewable resource bio-polymer. Chitin is found in exoskeletons of invertebrates. In a preferred embodiment, chitin is derived from the family of decapod crustaceans such as shrimp and prawns. Chitin obtained in this manner generally has a molecular weight of approximately between 500 and 900 kDalton. Process 10 is necessary to the present invention as chitin is insoluble.

The chitin is processed by removing non-chitin components in step 12. This step is accomplished in one embodiment through the use of hydrochloric acid (HCL). The HCL removes or strips any residual meat tissue that is attached to the shell. It is appreciated that other acids or methods of stripping the residual meat tissue can be incorporated without departing from the broad aspects of the present invention. After the residual meat tissue is stripped, a solution of Sodium Hydroxide (NaOH) is used to rinse and neutralize the exoskeletons. In the preferred embodiment, a NaOH solution of approximately 20% is used.

Step 13 involves drying the chitin and processing the chitin to have a desired size. Preferably, the chitin is ground so that it has an average size of approximately 24 mesh (0.0278 inches average particle dimension).

Step 14 is deacetylation. This step 14 involves in a preferred embodiment mixing 1 part chitin with 4 parts 50% NaOH, which is a base to which had been added 1 part of pure water. The resulting mixture comprises 5 parts total, of which the solution has 40% NaOH per 1 part chitin. The mixture is heated to approximately 70 degrees Celsius for about 72 hours to undergo the process of deacetylation. The process of deacetylation converts some of the N-acetyl glucosamine to glucosamine. The result of deacetylation is the aggregation and precipitation of chitosan molecules.

Step 15 is to rinse the chitosan to remove remaining NaOH and any other impurities. In the preferred embodiment, the step 15 of rinsing the chitosan comprises a triple rinse. Yet, it is appreciated that other numbers of rinses could alternatively be used without departing from the broad aspects of the present invention. It is preferable that the chitosan is then allowed to dry.

Turning now to FIG. 3, the step 20 of making a 2% chitosan solution is provided.

The following preferred embodiment yields approximately 1 liter, or 1000 mls of the chelated silver oxide complex. The first step (21) in this process (20) is to provide deionized water. 182 ml. of deionized water is measured and placed under moderate to high agitation. 20 grams of chitosan (rinsed and dried) is then provided in step (22), and measured. The chitosan powder is dispersed into and mixed with the deionized water under moderate to high agitation. Next, in step (23), an alpha-hydroxy acid such as glycolic acid is provided. In the preferred embodiment, glycolic acid is used for its lack of strong odor, and is of approximately 70% purity. It is understood that other alpha-hydroxy acids may be used without departing from the broad aspects of the present invention. Approximately 45 ml. of the glycolic acid can be added, and the mixture can be mixed slowly for approximately an additional 45 to 60 minutes. After this period of time, the mixture is preferably viscous. The chitosan solution is preferably ready when it achieves the desired viscosity.

Turning now to FIG. 4, a method (30) of preparing a silver oxide solution is provided. First, in step (31), silver salts can be provided. Primarily, the use of silver oxide in a powdered form is provided. Next, an alkaline aqueous solution of water and the silver oxide powder is provided in step (32). The result, in step (33), is the formation of silver oxide in the form of an aqueous alkaline solution. Once the silver oxide thin slurry is created and fully formed, citric acid can be provided together with the thicker chitosan solution (in step 34), and deionized water can be provided in step 36.

The following steps are utilized to yield a 1 liter, or 1000 ml batch of constituted 1000 ppm chelated silver oxide solution. Slurry 1 is prepared by adding approximately 1.10 grams chelated silver oxide to approximately 198.9 grams distilled water and dispersing for approximately 5-10 minutes. The dispersed chelated silver oxide in water Slurry 1 can be slowly added to a solution of the chitosan and citric acid to form a second solution (2) mixed at a high speed for approximately 30-45 minutes. The resulting silver oxide chelate is colorless and odorless. Remove from agitation, filter through a qualitative analysis filter paper, such as VWR, 415 and set aside in a light impervious container.

The silver is first dispersed in the distilled water to form a thin slurry so that there is a larger exposure of the surface area of the silver to form a silver oxide molecule which can combine with the citric acid. The $Ag_2O$ molecule is only slightly soluble in a solution, hence the addition of citric acid to the mixture also increases solubility with the chitosan to produce a silver ion portion of the silver oxide compound that forms a coordination compound as a result of a Lewis acid-base reaction. The silver ion here is the acid (acceptor) and the chitosan/citric acid solution acts as a ligand base (donor).

In particular the formed solution is a bio-film forming sanitizer that is cationic and bio-adhesive, and contains chelated silver oxide in a concentration sufficient to effect residual antibacterial activity for hours.

The following ratios are used in order to achieve a 1 liter batch, or 1000 ml. batch. First, in steps approximately 500 ml. of 2% chitosan solution and approximately 400 mls. of deionized water are provided which includes citric acid. The chitosan, citric acid and deionized water are preferably mixed slowly for approximately 3 minutes. Next, approximately 100 ml. of the 1000 ppm silver oxide solution is provided. The silver oxide solution is added to the chitosan solution and the solution is preferably mixed slowly for an additional 3 minutes. The resulting solution is a formulation containing 100 ppm silver oxide and bio-bonding chitosan. It is appreciated that all vessels and agitators in this method are made of high density plastic or glass, and must be free of metallic surfaces.

It is understood that other ratios of chitosan solution to silver oxide solution can be used without departing from the broad aspects of the present invention.

According to the present invention, the citrate is complexed with silver ions and silver oxide and chitosan, and the bacteria accordingly take up the silver oxide citrate chitosan complex. Unwanted bacteria, viruses, molds and fungi rapidly die after taking up the silver, as the silver immediately disables vital proteins and the bacteria's metabolic and reproductive functions and the organisms tend to die within minutes. This chelated silver oxide compound, however, provides biocompatibility with desirable cells and organisms such that there are no known toxic side effects when using the chelated silver oxide complex processed as detailed above.

The silver oxide complex is cationic and bonds readily to negatively charged human or animal skin without any toxic effects. The chitosan-silver oxide complex does not cause silver poisoning in a manner such as is known for many of the colloidal (ionic) silver compounds. This is due to the mechanism of the molecule itself. When absorbed into the skin, the complex immediately becomes inert as it binds with free sodium ions that occur naturally in our bodies and on our skin and the oxygen species acts as primarily to promote stable and healthy cell growth. The chelated silver oxide molecule is eventually excreted through the kidneys or out of the pores of the skin depending on the activity level of the individual.

Working Example 2

A 500 ml amount of polyol based complex suspension together with 100 ppm of a silver oxide complex was prepared in the following manner:
Solution A
0.265 gms. Citric Acid and add to
299.735 gms. Distilled Water with 2% chitosan solution
Mix 5-10 minutes
Slurry 1
0.11 gms. Silver Oxide and add to
99.89 gms. Distilled Water
Disperse 5-10 minutes
Take prepared Solution A and place under moderate agitation for the stipulated time. Slowly add the previously dispersed silver oxide in water Slurry 1 and mix at high speed for 30-45 minutes. The resulting silver oxide is a chelate and is colorless and odorless. Remove from agitation, filter through a qualitative analysis filter paper, such as VWR 20 415, and set aside in a light impervious container. The silver oxide complex is now ready to be used to make a glycerine composition useful for various purposes. Take 30 mls of the 2% chitosan solution and to it add 70 mls distilled water. Mix for 1 minute and then add to the 400 mls of the previously prepared 100 ppm chelated silver oxide complex. Mix all for 3 minutes and then add to al polyol such as propanediol and optionally propylene glycol as a non-precipitating complex suspension to be While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

We claim:

1. An antimicrobial, antibacterial, and/or anti-viral, composition comprising; chelated silver oxide particles suspended in a glycerine and water based liquid, wherein said chelated silver oxide particles are homogeneously dispersed in said glycerine and water liquid based composition and wherein said chelated silver oxide particles exist as a stable complex suspension in said glycerine and water liquid based composition such that a concentration of said chelated silver oxide particles of said stable complex suspension are in a concentration of at least 0.30 weight percent and remain suspended in said glycerine and water based liquid composition and wherein said stable complex suspension forms no precipitate and wherein said chelated metal oxide particles remain homogeneously suspended in said glycerine and water liquid based composition that is a chelated silver oxide complex suspension wherein said silver oxide complex suspension is a carrier combined with and infused into a polymer host that can be pelletized.

2. Articles of manufacture for antibacterial, antimicrobial, and/or antiviral products, wherein said articles comprise the composition of claim 1; wherein the chelated silver oxide complex is in a concentration of at least 0.001 weight percent silver oxide infused within said polymer such that said concentration of said chelated silver oxide complex is no greater than 25 weight percent of a polymeric host composition.

3. The articles of manufacture of claim 2, wherein said articles of manufacture are selected from the group consisting of: medical devices and hospital products, tubing, masks, mats, plastic cups, surgical instruments, catheters, cannulae, stents, guide wires, implant devices, contact lenses, IUDs, peristaltic pump chambers, endotracheal tubes, gastroenteric feeding tubes, arteriovenous shunts, condoms, oxygenator and kidney membranes, gloves, pacemaker leads, and wound dressings.

4. The articles of manufacture of claim 2, wherein said polymeric host composition reduces or eliminates bacteria without changing measurable physio-chemical properties of said polymeric host composition.

5. The articles of manufacture of claim 2, wherein said articles are selected from the group consisting of: toys, bottles, pacifiers, diaper creams and ointments and wound healing substances.

6. The articles of manufacture of claim 5, selected from the group consisting of: kitchen appliances, countertops and cutting boards.

7. The articles of manufacture of claim 2, selected from the group consisting of: household products, bathroom accessories, bathroom fixtures, flooring, cleaning products, air filtration items, food storage items, HVAC, luggage, antibacterial shower curtains and products for office and school usage.

8. The articles of manufacture of claim 2, selected from the group consisting of: sporting equipment mouthguards, mouthpieces, and dental appliances.

9. The articles of manufacture of claim 2, selected from the group consisting of: vacuum cleaners, water filters storage devices, aircraft interiors, baby changing stations, cleaning supplies, commercial high chairs, dispensers, door hardware, electronics, elevators, storage units, surface coatings, and transportation products.

10. The articles of manufacture of claim 2, selected from the group consisting of: automobile interiors, steering wheels and steering wheel covers, window handles, buttons, and dashboards.

11. The articles of manufacture of claim 2, selected from the group consisting of: yoga or other exercise and gymnastic or wrestler mats, mattresses, and handles for gym equipment.

12. The articles of manufacture of claim 2, selected from the group consisting of: water floatation devices, boats and boat interior/exterior surfaces, watercraft, and respective watercraft surfaces.

13. The articles of manufacture of claim 2, selected from the group consisting of: aircraft interiors, serving trays, air vents, and seats or seat coverings.

14. The articles of manufacture of claim 2, selected from the group consisting of: antibacterial and UV resistant window coverings, footwear, medical textiles, water and outdoor/indoor protective wear.

15. The articles of manufacture of claim 2, selected from the group consisting of: antibacterial toothbrushes, handles and bristles thereof.

16. The articles of manufacture of claim 2, selected from the group consisting of: communications devices, cell phones, personal computers, computer tablets and mobile, handheld, communications devices.

17. The articles of manufacture of claim 2, selected from the group consisting of: utensils, plastic forks, knives, and spoons.

* * * * *